United States Patent
Lafont et al.

(10) Patent No.: US 7,838,021 B2
(45) Date of Patent: Nov. 23, 2010

(54) PLATFORMS, PARTICULARLY PROSTHESES, HAVING BIOLOGICALLY ACTIVE COVERINGS

(75) Inventors: Antoine Lafont, Paris (FR); Ayman Al Hajzen, Issy les Moulineaux (FR)

(73) Assignee: Universite Paris 5, Paris Cedex (FR)

( * ) Notice: Subject to any disclaimer, the term of this patent is extended or adjusted under 35 U.S.C. 154(b) by 323 days.

(21) Appl. No.: 10/561,238

(22) PCT Filed: Jun. 18, 2004

(86) PCT No.: PCT/FR2004/001528

§ 371 (c)(1),
(2), (4) Date: Feb. 1, 2006

(87) PCT Pub. No.: WO2004/112861

PCT Pub. Date: Dec. 29, 2004

(65) Prior Publication Data

US 2007/0112406 A1      May 17, 2007

(30) Foreign Application Priority Data

Jun. 19, 2003   (FR)   .................................. 03 07395

(51) Int. Cl.
*A61F 2/02* (2006.01)
(52) U.S. Cl. ..................................................... 424/423
(58) Field of Classification Search ................. 424/423; 623/1.1
See application file for complete search history.

(56) References Cited

U.S. PATENT DOCUMENTS

| 5,650,389 | A | 7/1997 | Krumdieck et al. |
| 6,413,931 | B1 * | 7/2002 | Hook et al. ................. 514/2 |
| 6,579,978 | B1 | 6/2003 | Renier et al. |

FOREIGN PATENT DOCUMENTS

| WO | 00/40278 A | 7/2000 |
| WO | 01/43789 A | 6/2001 |

OTHER PUBLICATIONS

Fischer et al., "Local expression of bovine decorin by cell-mediated gene transfer reduces neointimal formation after balloon injury in rats", Circulation Research, vol. 86, No. 6, Mar. 31, 2000, pp. 676-683, XP002315415.
International Search Report of PCT/FR2004/001528, mailed Feb. 15, 2005.

* cited by examiner

*Primary Examiner*—Carlos A Azpuru
(74) *Attorney, Agent, or Firm*—Nixon & Vanderhye P.C.

(57) ABSTRACT

The invention relates to the use of extracellular matrix regulators for producing a pharmacologically active covering on a platform or a prosthesis. This covering is of application to endoluminal prostheses, preferably using decorine or a fragment or derivative thereof as cellular matrix inhibitor.

8 Claims, No Drawings

```
                        SEQUENCE LISTING

<160> NUMBER OF SEQ ID NOS: 1

<210> SEQ ID NO 1
<211> LENGTH: 359
<212> TYPE: PRT
<213> ORGANISM: Human

<400> SEQUENCE: 1

Met Lys Ala Thr Ile Ile Leu Leu Leu Ala Gln Val Ser Trp Ala
1               5                   10                  15

Gly Pro Phe Gln Gln Arg Gly Leu Phe Asp Phe Met Leu Glu Asp Glu
                20                  25                  30

Ala Ser Gly Ile Gly Pro Glu Val Pro Asp Asp Arg Asp Phe Glu Pro
            35                  40                  45

Ser Leu Gly Pro Val Cys Pro Phe Arg Cys Gln Cys His Leu Arg Val
        50                  55                  60

Val Gln Cys Ser Asp Leu Gly Leu Asp Lys Val Pro Lys Asp Leu Pro
65                  70                  75                  80

Pro Asp Thr Thr Leu Leu Asp Leu Gln Asn Asn Lys Ile Thr Glu Ile
                85                  90                  95

Lys Asp Gly Asp Phe Lys Asn Leu Lys Asn Leu His Ala Leu Ile Leu
                100                 105                 110

Val Asn Asn Lys Ile Ser Lys Val Ser Pro Gly Ala Phe Thr Pro Leu
            115                 120                 125

Val Lys Leu Glu Arg Leu Tyr Leu Ser Lys Asn Gln Leu Lys Glu Leu
        130                 135                 140

Pro Glu Lys Met Pro Lys Thr Leu Gln Glu Leu Arg Ala His Glu Asn
145                 150                 155                 160

Glu Ile Thr Lys Val Arg Lys Val Thr Phe Asn Gly Leu Asn Gln Met
                165                 170                 175

Ile Val Ile Glu Leu Gly Thr Asn Pro Leu Lys Ser Ser Gly Ile Glu
                180                 185                 190

Asn Gly Ala Phe Gln Gly Met Lys Lys Leu Ser Tyr Ile Arg Ile Ala
            195                 200                 205

Asp Thr Asn Ile Thr Ser Ile Pro Gln Gly Leu Pro Pro Ser Leu Thr
        210                 215                 220

Glu Leu His Leu Asp Gly Asn Lys Ile Ser Arg Val Asp Ala Ala Ser
```

-continued

```
225                 230                 235                 240
Leu Lys Gly Leu Asn Asn Leu Ala Lys Leu Gly Leu Ser Phe Asn Ser
                245                 250                 255

Ile Ser Ala Val Asp Asn Gly Ser Leu Ala Asn Thr Pro His Leu Arg
                260                 265                 270

Glu Leu His Leu Asp Asn Asn Lys Leu Thr Arg Val Pro Gly Gly Leu
            275                 280                 285

Ala Glu His Lys Tyr Ile Gln Val Val Tyr Leu His Asn Asn Asn Ile
            290                 295                 300

Ser Val Val Gly Ser Ser Asp Phe Cys Pro Pro Gly His Asn Thr Lys
305                 310                 315                 320

Lys Ala Ser Tyr Ser Gly Val Ser Leu Phe Ser Asn Pro Val Gln Tyr
                325                 330                 335

Trp Glu Ile Gln Pro Ser Thr Phe Arg Cys Val Tyr Val Arg Ser Ala
            340                 345                 350

Ile Gln Leu Gly Asn Tyr Lys
            355
```

PLATFORMS, PARTICULARLY PROSTHESES, HAVING BIOLOGICALLY ACTIVE COVERINGS

This application is the US national phase of international application PCT/FR2004/001528, filed 18 Jun. 2004, which designated the U.S. and claims benefit of FR 03/07395, filed 19 Jun. 2003, the entire contents of each of which are hereby incorporated by reference.

The subject of the invention is the use of biologically active compounds for the coating of platforms, in particular prostheses. It relates in particular to the coating of stents comprising a biologically active coating.

It is known that the treatment of stenoses of the coronary arteries was revolutionized by coronary angioplasty, which consists of opening the stenosis with a balloon. This technique was improved by using a metal arterial endoprosthesis, called a "stent", in order to prevent retractile cicatrization of the artery causing restenosis, i.e. the reappearance of the stenosis. However, in a good number of cases, varying from 20 to 40% depending on the type of lesion, it was found that the insertion of a stent in an artery causes a restenosis linked with a neointimal hyperplasia, which results both from an excess of scar tissue and from a reaction to the foreign body. In order to overcome these problems, it was proposed to coat the stents with medicated substances capable of combating restenoses.

Of the strategies proposed, that which consists of using molecules with cytotoxic or cytostatic effects aroused much interest. During the first 6 months of insertion of stents with a coating of cytotoxic or cytostatic compounds, no restenosis was observed.

However, these molecules have the drawback of also inhibiting the scarring phase, which produces a risk of late thrombosis on a bare metal body, as well as the creation of a space between the stent and the artery wall by dilatation of this wall (hereafter called positive remodelling).

On animal models, a late restenosis phenomenon was also observed.

It therefore transpires that, although the use of stents as pharmacological platforms allowing delivery of a medicament constitutes a beneficial approach, the therapeutic families proposed up until now are not satisfactory.

The inventors found that, by following another medication-based approach, based on the use of multi-functional compounds, it was possible to have a regulatory effect on the extracellular matrix, and to inhibit the scar tissue responsible for hyperplasia, thus preventing intra-stent restenosis. This result proved to be applicable generally to the coating of other prostheses in other medical indications, and in general to any biological platform.

The invention is therefore based on a multiple-effect strategy aimed at cell proliferation and migration, the metabolism of the extracellular matrix and control of inflammation.

The aim of the invention is therefore to use novel compounds in the development of coatings for platforms, in particular prostheses.

It also relates, as new products, to these platforms and prostheses, in particular stents having such coatings.

The use according to the invention is characterized by the use of multi-functional compounds to develop a pharmacologically active coating on a platform/prosthesis.

Surprisingly, such coatings make it possible, in a situation of mechanical trauma of the tissues causing an inflammatory response, to avert arterial restenosis.

Unlike the prior art strategies mentioned above, such regulators do not affect the cell cycle and therefore do not have a deleterious effect on the endothelium which may result in the appearance of late thromboses, a positive remodelling or a late restenosis.

It is thus possible to keep a healthy wall which is not adversely affected by the loss of or damage to cells, which also allows thrombosis phenomena to be averted.

Preferably, decorin and/or a peptide fragment of decorin, or the derivatives of decorin and/or of a fragment of decorin, possessing the properties of these compounds but chemically modified in order to give them advantageous properties for a given application, are used.

Human decorin is a protein comprising 359 amino acids with a chain of glycosaminoglycans, with a molecular weight of 100 to 120 kDa. It corresponds to the following sequence:

```
mkatiillll aqvswagpfq qrglfdfmle deasgigpev
pddrdfepsl gpvcpfrcqc hlrvvqcsdl gldkvpkdlp
pdttlldlqn nkiteikdgd fknlknlhal ilvnnkiskv
spgaftplvk lerlylsknq lkelpekmpk tlqelrahen
eitkvrkvtf nglnqmivie lgtnplkssg iengafqgmk
klsyiriadt nitsipqglp psltelhldg nkisrvdaas
lkglnnlakl glsfnsisav dngslantph lrelhldnnk
ltrvpgglae hkyiqvvylh nnnisvvgss dfcppghntk
kasysgvslf snpvqyweiq pstfrcvyvr saiqlgnyk
```

The decorin used according to the invention advantageously corresponds to the following domains:

Domain I: Signal peptide+propeptide,

Domain II: Cysteine residues+glycosaminoglycans (GAGs) attachment site

Domain III: Leucine-rich repeats (LRR), protein core (38-43 kDa),

Domain IV: Cysteine residues with loop.

The active protein fragment alternatively proposed is defined as follows: bioactive decorin fragment between the amino acid in positions (115) and (260), 15-20 kDa.

The presence of these compounds on a platform allows their multi-functional properties to be exploited. It is thus possible to act on cell proliferation (by inhibiting the action of PDGF and of EGF, by binding on the EGF receptor), on cell migration (by inhibiting migration by action on fibronectin and thrombospondin, and by inhibiting degradation of the extracellular matrix), on inflammation (by reducing the infiltration of macrophages; by inhibiting the inflammatory action of interleukin 1 and the inflammatory response to angioplasty trauma on the smooth muscular cells by maintaining their contractile phenotype (which does not secrete extracellular matrix and pro-inflammatory cytokines)), and by acting against fibrosis (by inhibiting the accumulation of the extracellular matrix, in particular via its action on interleukin 1, TGFβ-1 and PDGF BB).

According to another feature, the invention also relates, as novel products, to platforms and prostheses, characterized in that they comprise a coating containing a therapeutically effective quantity of at least one compound as defined above.

By therapeutically effective quantity is meant a quantity which allows the effects mentioned above to be obtained, especially regulation, in particular the inhibition of the surplus of extracellular matrix produced in response to the trauma of the inserted platform or prosthesis. Quantities of the order of 10 to 100 µg/mm$^2$ proved to be appropriate.

Preferred platforms and prostheses more particularly contain a therapeutically effective quantity of decorin and/or of a peptide fragment of decorin, and/or of a derivative of decorin or of a fragment of decorin.

These compounds are bound directly to the platform or prosthesis, or via a biostable or biodegradable coating such as a lactic acid polymer. The binding of the compounds can be reversible or irreversible. The platforms or prostheses can be biodegradable, for example made of lactic acid polymer. They can be also made of manganese. The release can either not take place, or take place at a speed which depends on the coating, the binding used, the platform (degradable or not).

The prostheses which are more specifically concerned correspond to implantable devices or endoluminal prostheses, in particular endovascular, urological, respiratory or digestive prostheses.

The antifibrotic effect of decorin and of a fragment of decorin is advantageously also exploited with prostheses outside arterial application, in particular in urological, digestive, bronchopulmonary applications.

In these applications, the compounds used are bound to a platform which is for example made of metal, or is bioresorbable. This binding can be temporary or permanent. The compound then acts in the proximity of the platform, this zone being at the source of the triggering of the greatest inflammation and therefore of the cell proliferation and migration, and the extracellular matrix accumulation.

Other characteristics and advantages of the invention are given in the following examples.

Production of Stents with a Bioactive Coating of Decorin and Arterial Application Operating according to standard techniques, a biostable or biodegradable coating based on polymers, for example a lactic acid polymer, containing a pharmacologically active quantity of decorin, allowing the release of active ingredient over 30 days, is applied to a metal stent for example made of 316L steel.

In vivo, the decorin locally inhibits restenosis in the iliac artery of rabbits. After 2 months of observations, no restenosis phenomenon was observed.

By way of a variant, the decorin is bound directly to the stent without a coating.

The invention claimed is:

1. A method for producing a biological platform containing a pharmacologically active coating, said method comprising applying to at least a portion of a surface of a biological platform an inhibitor of synthesis of an extracellular matrix, of cell proliferation and migration, and of inflammation, to produce said biological platform containing a pharmacologically active coating, said inhibitor being a decorin peptide or biologically active fragment of decorin selected from the group consisting of (a) a decorin peptide comprising signal peptide and propeptide, (b) a 15-20 kDa biologically active fragment of decorin comprising amino acids 115 to 260 of decorin, (c) a biologically active fragment of decorin comprising a leucine-rich repeat, protein core (38-43 kDa) sequence of decorin and (d) a biologically active fragment of decorin comprising a decorin loop structure formed from cysteine residues.

2. A method for producing a biological platform containing a pharmacologically active coating, said method comprising applying to at least a portion of a surface of a biological platform an inhibitor of synthesis of an extracellular matrix, of cell proliferation and migration, and of inflammation, to produce said biological platform containing a pharmacologically active coating, said inhibitor being a decorin peptide or biologically active fragment of decorin selected from the group consisting of (a) a decorin peptide comprising signal peptide and propeptide, (b) a 15-20 kDa biologically active fragment of decorin comprising amino acids 115 to 260 of decorin, (c) a biologically active fragment of decorin comprising a leucine-rich repeat, protein core (38-43 kDa) sequence of decorin (d) a biologically active fragment of decorin comprising a decorin loop structure formed from cysteine residues, (e) a chemically modified derivative of (a) which is biologically active, (f) a chemically modified derivative of (b) which is biologically active, (g) a chemically modified derivative of (c) which is biologically active, and (h) a chemically modified derivative of (d) which is biologically active.

3. An endoluminal prostheses comprising a surface coating of a therapeutically effective quantity of a decorin peptide or biologically active fragment of decorin selected from the group consisting of (a) a decorin peptide comprising signal peptide and propeptide, (b) a 15-20 kDa biologically active fragment of decorin comprising amino acids 115 to 260 of decorin, (c) a biologically active fragment of decorin comprising a leucine-rich repeat, protein core (38-43 kDa) sequence of decorin and (d) a biologically active fragment of decorin comprising a decorin loop structure formed from cysteine residues.

4. A stent comprising a surface coating of a therapeutically effective quantity of a decorin peptide or biologically active fragment of decorin selected from the group consisting of (a) a decorin peptide comprising signal peptide and propeptide, (b) a 15-20 kDa biologically active fragment of decorin comprising amino acids 115 to 260 of decorin, (c) a biologically active fragment of decorin comprising a leucine-rich repeat, protein core (38-43 kDa) sequence of decorin and (d) a biologically active fragment of decorin comprising a decorin loop structure formed from cysteine residues.

5. The method of claim 1 wherein said biological platform is a prosthesis.

6. The method of claim 2 wherein said biological platform is a prosthesis.

7. An endoluminal prostheses comprising a surface coating of a therapeutically effective quantity of a decorin peptide or biologically active fragment of decorin selected from the group consisting of (a) a decorin peptide comprising signal peptide and propeptide, (b) a 15-20 kDa biologically active fragment of decorin comprising amino acids 115 to 260 of decorin, (c) a biologically active fragment of decorin comprising a leucine-rich repeat, protein core (38-43 kDa) sequence of decorin (d) a biologically active fragment of decorin comprising a decorin loop structure formed from cysteine residues, (e) a chemically modified derivative of (a) which is biologically active, (f) a chemically modified derivative of (b) which is biologically active, (g) a chemically modified derivative of (c) which is biologically active, and (h) a chemically modified derivative of (d) which is biologically active.

8. A stent comprising a surface coating of a therapeutically effective quantity of a decorin peptide or biologically active fragment of decorin selected from the group consisting of (a)

a decorin peptide comprising signal peptide and propeptide, (b) a 15-20 kDa biologically active fragment of decorin comprising amino acids 115 to 260 of decorin, (c) a biologically active fragment of decorin comprising a leucine-rich repeat, protein core (38-43 kDa) sequence of decorin (d) a biologically active fragment of decorin comprising a decorin loop structure formed from cysteine residues, (e) a chemically modified derivative of (a) which is biologically active, (f) a chemically modified derivative of (b) which is biologically active, (g) a chemically modified derivative of (c) which is biologically active, and (h) a chemically modified derivative of (d) which is biologically active.

* * * * *